US00PP10756P

United States Patent [19]

Gutierrez

[11] Patent Number: Plant 10,756

[45] Date of Patent: Jan. 12, 1999

[54] AGLAONEMA PLANT NAMED 'ILLUMINATION'

[75] Inventor: Romeo R. Gutierrez, Quezon City, Philippines

[73] Assignee: Sunshine Foliage World, Zolfo Springs, Fla.

[21] Appl. No.: 923,733

[22] Filed: Sep. 4, 1997

[51] Int. Cl.[6] ..... A01H 5/00

[52] U.S. Cl. ..... Plt./88.1

[58] Field of Search ..... Plt./88.1

*Primary Examiner*—Howard J. Locker

*Assistant Examiner*—Kent L. Bell

*Attorney, Agent, or Firm*—C. A. Whealy

[57] ABSTRACT

A new and distinct cultivar of Aglaonema named 'Illumination' particularly characterized by its outwardly arching growth habit; glossy silver green upper leaf surfaces with dark green, yellowish green and white spots and streaks; white petioles; tolerance to low temperatures; and resistance to diseases common to Aglaonema.

1 Drawing Sheet

The present invention relates to a new and distinct cultivar of Aglaonema plant, botanically known as *Aglaonema nitidum* var. *nitidum* f. *curtisii* ×*Aglaonema marantifolium tricolor* and hereinafter referred to by the cultivar name 'Illumination'.

The new Aglaonema is a product of a planned breeding program conducted by the inventor in Quezon City, The Philippines. The new Aglaonema originated from a cross made by the inventor of the nonpatented *Aglaonema nitidum* var. *nitidum* f. *curtisii* cultivar 'Jeannie' as the female, or seed, parent with an unnamed plant of *Aglaonema marantifolium tricolor* as the male, or pollen, parent. The cultivar 'Illumination' was discovered and selected by the inventor as a seedling within the progeny of the stated cross in a controlled environment in Quezon City, The Philippines in August, 1986.

Plants of the new Aglaonema differ from plants of the parents, *Aglaonema nitidum* var. *nitidum* f. *curtisii* cultivar 'Jeannie' and *Aglaonema marantifolium tricolor*, in petiole color, leaf color and leaf markings.

Asexual propagation of the new cultivar by divisions at Quezon City, The Philippines, and Zolfo Springs, Fla., has shown that the unique features of this new Aglaonema plant are stable and reproduced true to type in successive generations.

The new Aglaonema has not been observed under all possible environmental conditions. The phenotype may vary somewhat with variations in environment such as temperature, light intensity, fertilizer rate, and/or irrigation amount and frequency without, however, any variance in genotype.

The following traits have been repeatedly observed and are determined to be the unique characteristics of 'Illumination'. These characteristics in combination distinguish 'Illumination' as a new and distinct cultivar:

1. Plants of the new Aglaonema are outwardly arching in growth.
2. The upper surfaces of mature leaves of plants of the new Aglaonema are glossy silver green with dark green, yellowish green and white spots and streaks.
3. The leaves of the new Aglaonema are relatively long.
4. Mature leaves of plants of the new Aglaonema have white petioles.
5. Plants of the new Aglaonema are tolerant of low temperatures, that is, ambient temperatures of about 8° C. do not cause foliar damage.
6. Plants of the new Aglaonema are resistant to diseases common to Aglaonema.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical single plant of 'Illumination' in a 25-cm container.

The photograph at the bottom of the sheet comprises a close-up view of the upper surfaces of a young leaf (top) and fully mature leaf (bottom). Leaf colors in the photographs may appear different from the actual colors due to light reflectance.

DETAILED BOTANICAL DESCRIPTION

The following observations, measurements and comparisons describe plants grown in Zolfo Springs, Fla., under a polypropylene-covered shadehouse and conditions which closely approximate those used in horticultural practice. Plants were grown under day temperatures ranging from 21 to 38° C. and night temperatures ranging from 7 to 21° C. The polypropylene shade provided a 84 percent decrease in ambient light level. In the following description, color references are made to The Royal Horticultural Society Colour Chart except where general terms of ordinary dictionary significance are used.

Botanical classification: *Aglaonema nitidum* var. *nitidum* f. *curtisii*×*Aglaonema marantifolium tricolor* cultivar 'Illumination'.

Parentage:

*Female, or seed, parent.*—*Aglaonema nitidum* var. *nitidum* f. *curtisii* cultivar 'Jeannie', not patented.

*Male, or pollen, parent.*—An unnamed plant of *Aglaonema marantifolium tricolor*.

Propagation:

*Type.*—By division and by cuttings.

*Time to initiate roots.*—About 28 and 60 days at 270 and 10° C., respectively.

*Time to develop roots.*—About 37 and 94 days at 270 and 10° C., respectively.

*Rooting habit.*—Numerous thick, fleshy, white roots.

Plant description:

*Plant shape.*—Outwardly arching and spreading, mounded habit, symmetrical. Closely-spaced leaves give plants a full and dense appearance.

*Growth habit.*—Erect when young, becoming more outwardly arching and spreading. Appropriate for 25-cm containers.

*Plant size.*—Height, soil surface to top of leaf canopy: About 55 cm. Width: About 80 cm.

*Plant vigor.*—Moderate.

*Stem description.*—Diameter at soil surface: About 2.5 cm. Internode length: About 2.5 cm. Color, mature: Dark yellowish green.

*Foliage description.*—Leaf shape: Oblong. Leaf length, fully expanded: About 29.5 cm. Leaf width, fully expanded: About 11 cm. Margin: Entire. Leaf tip: Acuminate. Leaf base: Cuneate. Leaf aspect: Mostly flat. Leaf texture: Leathery, smooth, glabrous, glossy on both surfaces. Leaf color:

Young, upper surface:

Background: Closest to 138B to 147B. Dark green spots/streaks: 144A to greener than 147A. Yellowish green spots/streaks: 150A/150B/150C. White spots/streaks: 155D and 150D. Young, lower surface: Background: 146B/146C. White spots/streaks: 155D. Mature, upper surface: Background: Closest to 191A. Dark green spots/streaks: 147A to darker than 147A. Light green and yellowish green spots/streaks: 144A, 154A, and 150A/150B/150C. White spots/streaks: 155D and 150D. Mature, lower surface: Background: Close to 146A/146B. White spots/streaks: 155D. Petiole length, primary shoot: About 22 cm. Petiole diameter at apex: About 6 mm. Petiole diameter at base: About 1.5 cm. Petiole wing: Apparent on lower 67% of mature leaf petiole, about 14 cm in length and about 8.5 cm in width. Petiole color: Young: White, 155D, with green, 144B. Mature: Mostly white, 155D. Venation: Mature, upper surface: Midvein: White, 155D, at base to yellowish green at apex. Lateral veins: Same as leaf color. Mature, lower surface: Midvein: White, 155D. Lateral veins: Same as leaf color.

*Inflorescence.*—Typical of Aglaonema, no commercial significance.

Disease tolerance: Plants of the new Aglaonema are exceptionally resistant to diseases common to Aglaonema.

Low temperature tolerance: Plants of the new Aglaonema are tolerant of low temperatures, that is, ambient temperatures of about 8° C. do not cause damage.

It is claimed:

1. A new and distinct cultivar of Aglaonema plant named 'Illumination', as illustrated and described.

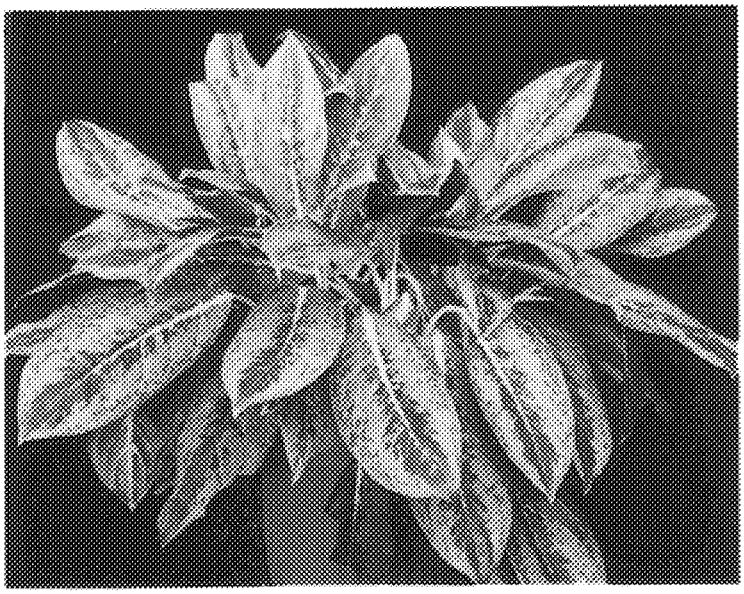
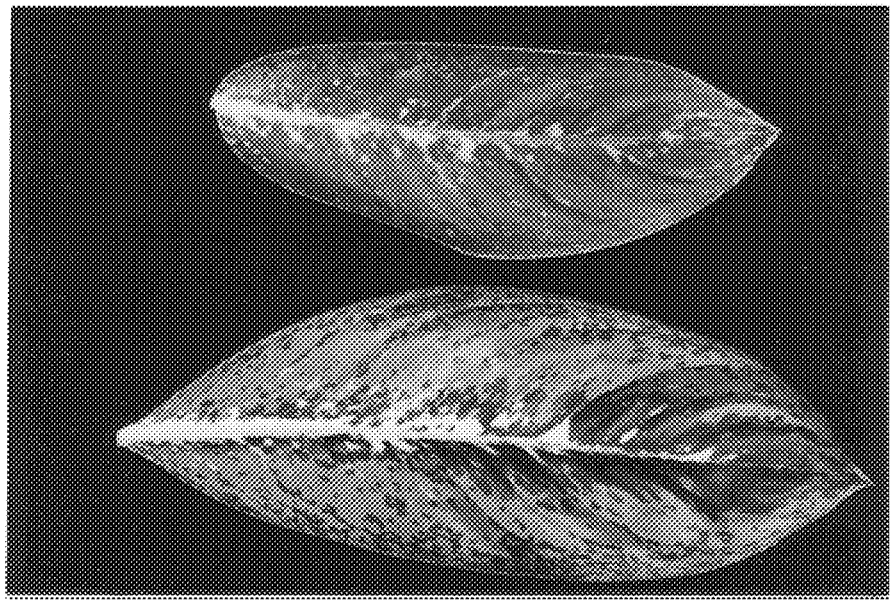

* * * * *